(12) United States Patent
Baril et al.

(10) Patent No.: US 10,758,245 B2
(45) Date of Patent: Sep. 1, 2020

(54) CLIP COUNTING MECHANISM FOR SURGICAL CLIP APPLIER

(71) Applicant: Covidien LP, Mansfield, MA (US)

(72) Inventors: Jacob C. Baril, White Plains, NY (US); Matthew A. Dinino, Newington, CT (US)

(73) Assignee: COVIDIEN LP, Mansfield, MA (US)

( * ) Notice: Subject to any disclaimer, the term of this patent is extended or adjusted under 35 U.S.C. 154(b) by 259 days.

(21) Appl. No.: 16/042,084

(22) Filed: Jul. 23, 2018

(65) Prior Publication Data

US 2019/0076148 A1 Mar. 14, 2019

Related U.S. Application Data

(60) Provisional application No. 62/557,778, filed on Sep. 13, 2017.

(51) Int. Cl.
| | | |
|---|---|---|
| *A61B 17/128* | (2006.01) | |
| *A61B 90/00* | (2016.01) | |
| *A61B 17/00* | (2006.01) | |

(52) U.S. Cl.
CPC ...... *A61B 17/1285* (2013.01); *A61B 2017/00407* (2013.01); *A61B 2090/0803* (2016.02)

(58) Field of Classification Search
CPC ...... A61B 17/128–1285; A61B 17/068; A61B 17/07207
See application file for complete search history.

(56) References Cited

U.S. PATENT DOCUMENTS

| | | |
|---|---|---|
| 3,120,230 A | 2/1964 | Skold |
| 3,363,628 A | 1/1968 | Wood |
| 3,638,847 A | 2/1972 | Noiles et al. |

(Continued)

FOREIGN PATENT DOCUMENTS

| | | |
|---|---|---|
| AU | 2013254887 A1 | 11/2013 |
| CA | 1163889 A | 3/1984 |

(Continued)

OTHER PUBLICATIONS

Extended European Search Report corresponding to Patent Application EP 18154617.7 dated Jun. 25, 2018.

(Continued)

*Primary Examiner* — Katrina M Stransky
*Assistant Examiner* — Brigid K Byrd

(57) ABSTRACT

A clip counting mechanism for use with a surgical clip applier includes a display gear rotatably supported within a handle housing of the surgical clip applier and including an outer surface having a plurality of numbers disposed thereon, a biasing element in mechanical communication with the display gear and rotatably biasing the display gear, a counter switch reciprocally disposed within the handle housing and defining a cam slot therethrough, and an escapement gear rotatably supported within the handle housing and defining a proximal end portion in mechanical communication with the display gear and a distal end portion in mechanical communication with the cam slot. Translation of the counter switch causes the cam slot to cam the escapement gear and selectively disengage and then re-engage the display gear to enable the display gear to rotate a predetermined angle of rotation.

20 Claims, 9 Drawing Sheets

(56) References Cited

U.S. PATENT DOCUMENTS

| | | |
|---|---|---|
| 3,675,688 A | 7/1972 | Bryan et al. |
| 3,735,762 A | 5/1973 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A * | 11/1994 | Slater ................ A61B 1/00062 116/216 |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |

(56) References Cited

U.S. PATENT DOCUMENTS

| | | |
|---|---|---|
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan |
| 6,546,935 B2 | 4/2003 | Hooven |
| 6,551,333 B2 | 4/2003 | Kuhns et al. |

(56) References Cited

U.S. PATENT DOCUMENTS

| | | |
|---|---|---|
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |

(56) References Cited

U.S. PATENT DOCUMENTS

| | | |
|---|---|---|
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |

(56) References Cited

U.S. PATENT DOCUMENTS

| | | |
|---|---|---|
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,228 B2 * | 6/2016 | Straehnz ............ A61B 17/0682 |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santini et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0085015 A1 | 4/2006 | Whitfield et al. |
| 2006/0100649 A1 | 5/2006 | Hart |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |

(56) References Cited

U.S. PATENT DOCUMENTS

| | | |
|---|---|---|
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2014/0074143 A1 | 3/2014 | Fitzgerald et al. |
| 2014/0263565 A1 | 9/2014 | Lytle, IV et al. |
| 2014/0276970 A1 | 9/2014 | Messerly et al. |
| 2015/0032131 A1 | 1/2015 | Sorrentino et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0030045 A1* | 2/2016 | Malkowski .......... A61B 17/128 606/143 |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | |
|---|---|---|
| CN | 104605911 B | 2/2017 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 1769757 A1 | 4/2007 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |

OTHER PUBLICATIONS

Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.

(56) References Cited

OTHER PUBLICATIONS

Chinese First Office Action corresponding to Patent Application CN 201510696298.9 dated Dec. 3, 2018.
Extended European Search Report corresponding to Patent Application EP 18158143.0 dated Dec. 5, 2018.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
European Office Action corresponding to EP 12 152 989.5 dated May 4, 2015.
Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024.1 dated Jul. 17, 2015.
Extended European Search Report corresponding to Int'l Application No. EP 14 19 2026.4 dated Jul. 17, 2015.
Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.
Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.

Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.
International Search Report dated Jan. 7, 2019 issued in corresponding PCT Appln. No. PCT/US2018/050336.
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).

(56) References Cited

OTHER PUBLICATIONS

The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.

\* cited by examiner

CLIP COUNTING MECHANISM FOR SURGICAL CLIP APPLIER

CROSS-REFERENCE TO RELATED APPLICATIONS

This application claims the benefit of and priority to U.S. Provisional Patent Application No. 62/557,778 filed Sep. 13, 2017, the entire disclosure of which is incorporated by reference herein.

BACKGROUND

Technical Field

The present disclosure relates generally to surgical clip appliers. More particularly, the present disclosure relates to endoscopic surgical clip appliers having a mechanism for indicating the number of remaining clips.

Description of Related Art

Endoscopic surgical staplers and surgical clip appliers are used for a number of minimally invasive or endoscopic surgical procedures. Typically in a minimally invasive surgical procedure, a tube or cannula device is extended into the patient's body through an entrance incision to provide an access port. The port allows the surgeon to insert a number of different surgical instruments therethrough for performing surgical procedures far removed from the incision.

During a majority of these procedures, the surgeon will need to terminate the flow of blood or other fluids through one or more vessels within or near the surgical site. To terminate the flow of blood or fluid through these vessels, a surgical clip applier is often used to ligate the necessary vessels. As can be appreciated, these surgical clip appliers are only able to store a finite number of surgical clips therein. Therefore, surgeons are often unable to ascertain how many surgical clips remain within a clip cartridge of the surgical clip applier during a surgical procedure.

Accordingly, a need exists for surgical clip appliers that provide a clinician with a convenient way to determine the number of surgical clips remaining within a surgical clip applier.

SUMMARY

The present disclosure relates to surgical clip appliers having a mechanism for indicating the number of remaining clips.

According to an aspect of the present disclosure, a clip counting mechanism for use with a surgical clip applier includes a display gear, a biasing element, a counter switch, and an escapement gear. The display gear is rotatably supported within a handle housing of the surgical clip applier and includes an outer surface having a plurality of numbers disposed therein. The biasing element is in mechanical communication with the display gear and rotatably biases the display gear. The counter switch is reciprocally disposed within the handle housing and defines proximal and distal end portions and opposed side surfaces extending therebetween. The opposed side surfaces define a cam slot therethrough. The escapement gear is rotatably supported within the handle housing and defines a proximal end portion and a distal end portion. The distal end portion is in mechanical communication with the cam slot of the counter switch and the proximal end portion is in mechanical communication with the display gear. Translation of the counter switch causes the cam slot to cam the escapement gear and selectively disengage the display gear and permit the display gear to rotate and selectively re-engage the display gear to inhibit rotation of the display gear, thereby enabling the display gear to rotate a predetermined angle of rotation.

In aspects, the outer surface of the display gear may define a plurality of ratchet teeth thereon.

In other aspects, the escapement gear may define a pair of arms disposed in juxtaposed relation wherein each arm of the pair of arms defines respective first and second teeth. In certain aspects, the first and second teeth may be configured to selectively engage a respective tooth of the plurality of ratchet teeth.

In aspects, the plurality of ratchet teeth may include 15 teeth such that the pre-determined angle of rotation of the display gear is 24 degrees. In certain aspects, translation of the counter switch in a first direction may cause the display gear to rotate 12 degrees in a first direction. In other aspects, translation of the counter switch in a second direction may cause the display gear to rotate a further 12 degrees in the first direction.

In certain aspects, each 24 degree rotation of the display gear in the first direction may cause a different number of the plurality of numbers to be displayed to a clinician, where the number displayed to the clinician is a number of surgical clips remaining in the surgical clip applier.

In some aspects, the clip counting mechanism may include a gear pin fixedly secured to the escapement gear and configured to be slidably received within the cam slot of the counter switch such that translation of the counter switch cams the gear pin within the cam slot and causes the escapement gear to rotate.

In aspects, the biasing element may be a constant-force spring.

According to another aspect of the present disclosure, an endoscopic surgical clip applier includes an endoscopic assembly and a handle assembly. The handle assembly includes a housing selectively connectable to the endoscopic assembly, a trigger pivotally connected to the housing, a drive bar translatably disposed within the housing of the handle assembly and operably coupled to the trigger, and a clip counting mechanism. The clip counting mechanism includes a display gear, a biasing element, a counter switch, and an escapement gear. The display gear is rotatably supported within a handle housing of the surgical clip applier and includes an outer surface having a plurality of numbers disposed therein. The biasing element is in mechanical communication with the display gear and rotatably biases the display gear. The counter switch is reciprocally disposed within the handle housing and defines proximal and distal end portions and opposed side surfaces extending therebetween. The opposed side surfaces define a cam slot therethrough. The escapement gear is rotatably supported within the handle housing and defines a proximal end portion and a distal end portion. The distal end portion is in mechanical communication with the cam slot of the counter switch and the proximal end portion is in mechanical communication with the display gear. Translation of the counter switch causes the cam slot to cam the escapement gear and selectively disengage the display gear and permit the display gear to rotate and selectively re-engage the display gear to inhibit rotation of the display gear, thereby enabling the display gear to rotate a predetermined angle of rotation.

In aspects, the outer surface of the display gear may define a plurality of ratchet teeth thereon.

In other aspects, the escapement gear may define a pair of arms disposed in juxtaposed relation wherein each arm of the pair of arms defines respective first and second teeth. In certain aspects, the first and second teeth may be configured to selectively engage a respective tooth of the plurality of ratchet teeth.

In aspects, the plurality of ratchet teeth may include 15 teeth such that the pre-determined angle of rotation of the display gear is 24 degrees. In certain aspects, translation of the counter switch in a first direction may cause the display gear to rotate 12 degrees in a first direction. In other aspects, translation of the counter switch in a second direction may cause the display gear to rotate a further 12 degrees in the first direction.

In certain aspects, each 24 degree rotation of the display gear in the first direction may cause a different number of the plurality of numbers to be displayed to a clinician, where the number displayed to the clinician is a number of surgical clips remaining in the surgical clip applier.

In some aspects, the clip counting mechanism may include a gear pin fixedly secured to the escapement gear and configured to be slidably received within the cam slot of the counter switch such that translation of the counter switch cams the gear pin within the cam slot and causes the escapement gear to rotate.

In aspects, the biasing element may be a constant-force spring.

BRIEF DESCRIPTION OF THE DRAWINGS

Particular embodiments of surgical clip appliers are described herein with reference to the drawings wherein.

DETAILED DESCRIPTION OF EMBODIMENTS

Figure 1:
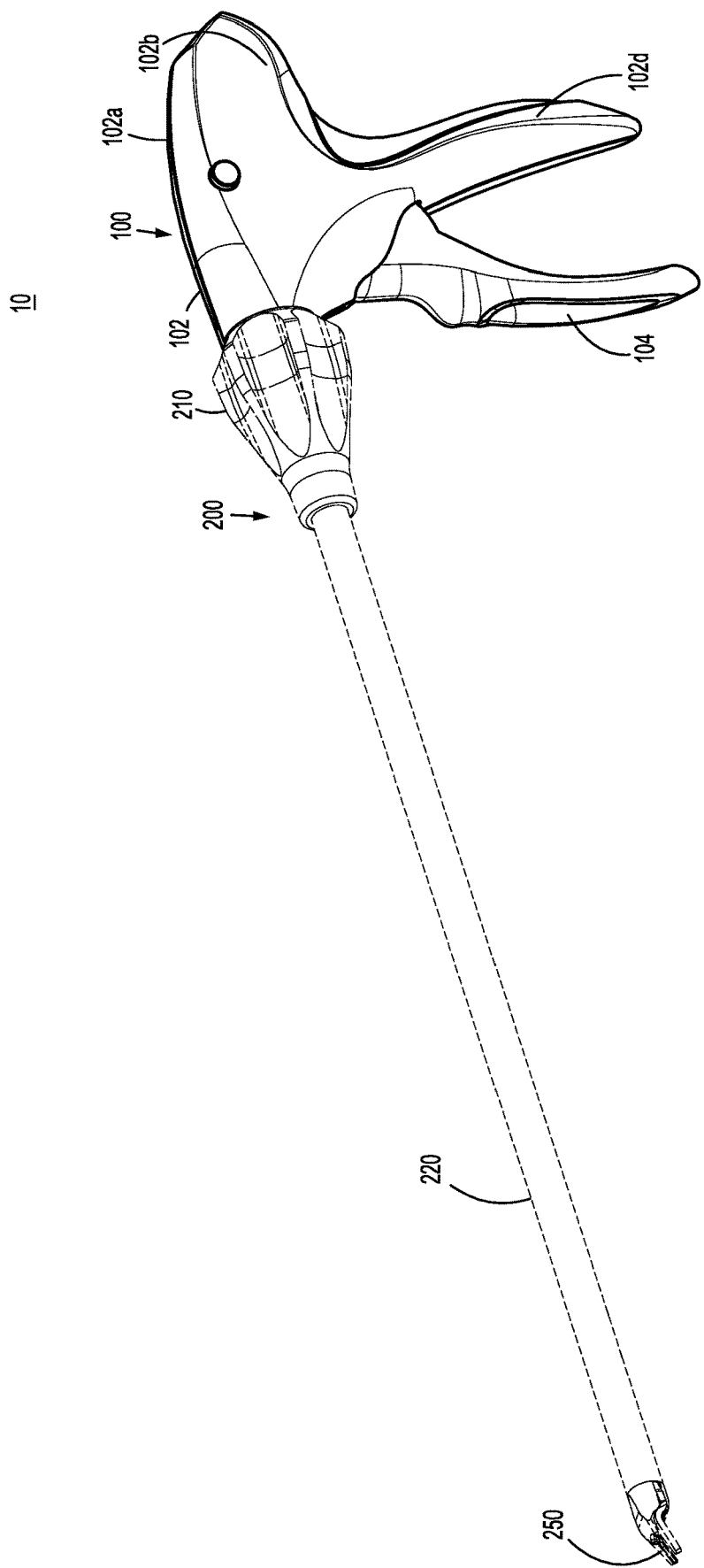
FIG. 1 is a perspective view of an endoscopic surgical clip applier, according to the present disclosure including an endoscopic assembly and a handle assembly.

In accordance with the present disclosure, an endoscopic surgical clip applier including a clip counting mechanism is provided. Although disclosed for use in an endoscopic surgical clip applier, the clip counting mechanism is usable in a wide variety of surgical clip appliers. The clip counting mechanism is disposed within a handle assembly of an endoscopic surgical clip applier and includes a display gear, a counter switch, an escapement gear, and a gear pin. The display gear is rotatably disposed about a display gear post of the handle assembly and is rotatably biased by a biasing element mechanically coupled to each of the display gear and the display gear post. The display gear defines an outer surface having a contrasting color disposed on a portion thereof to indicate that the number of remaining surgical clips is low. The outer surface of the display gear defines a plurality of ratchet teeth that are radially spaced apart such that each tooth represents a predetermined angle of rotation, which in embodiments is 24 degrees. The outer surface of the display gear includes a plurality of numbers disposed thereon and sequentially arranged thereon such that as the display gear rotates, the number of the plurality of numbers that is displayed to the clinician decreases with each firing of a surgical clip.

The counter switch defines a generally planar configuration having a laterally extending tab defined on a distal end thereof. The laterally extending tab is configured to selectively engage a protrusion of a drive bar such that translation of the drive bar in a distal direction effectuates a corresponding distal translation of the counter switch. An upper surface of the counter switch defines a vertically extending tab that is configured to selectively engage a drive bar pin of the handle assembly such that proximal translation of the drive bar, and therefore the drive bar pin, effectuates a corresponding proximal translation of the counter switch. A proximal portion of the counter switch defines a slot having a generally dog leg configuration that is configured to slidably engage the gear pin and cam the gear pin as the counter switch translates relative thereto.

The escapement gear defines a generally crescent wrench shape having a C-shaped proximal portion and a linearly extending distal portion. The proximal portion of the escapement gear defines a pair of opposed arms in juxtaposed relation, each defining a respective tooth configured to selectively engage a corresponding tooth of the plurality of ratchet teeth of the drive gear. The escapement gear is rotatably supported on a escapement gear boss defined on the housing of the endoscopic surgical clip applier. The gear pin is fixedly supported by the escapement gear such that translation of the counter switch causes the gear pin to cam within the cam slot of the counter switch. Distal translation of the counter switch effectuates clockwise rotation of the escapement gear and a release of the display gear from a tooth of the escapement gear such that the display gear rotates in a clockwise direction. Continued distal translation of the counter switch causes the gear pin to cam within the cam slot until an opposite tooth of the escapement gear engages a corresponding tooth of the display gear, stopping rotation of the display gear. After forming the surgical clip, retraction of the counter switch causes the gear pin to cam in an opposite direction and rotate the escapement gear in a counter-clockwise direction. Continued counter-clockwise rotation of the escapement gear releases the display gear and permits the display gear to further rotate in a clockwise direction until the escapement gear rotates further and engages another tooth of the display gear to stop rotation thereof. The clockwise rotation of the display gear causes the number of the plurality of numbers disposed on the display gear to decrease by one, until no surgical clip remain.

Embodiments of endoscopic surgical clip appliers and clip counting mechanisms, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Figure 2:
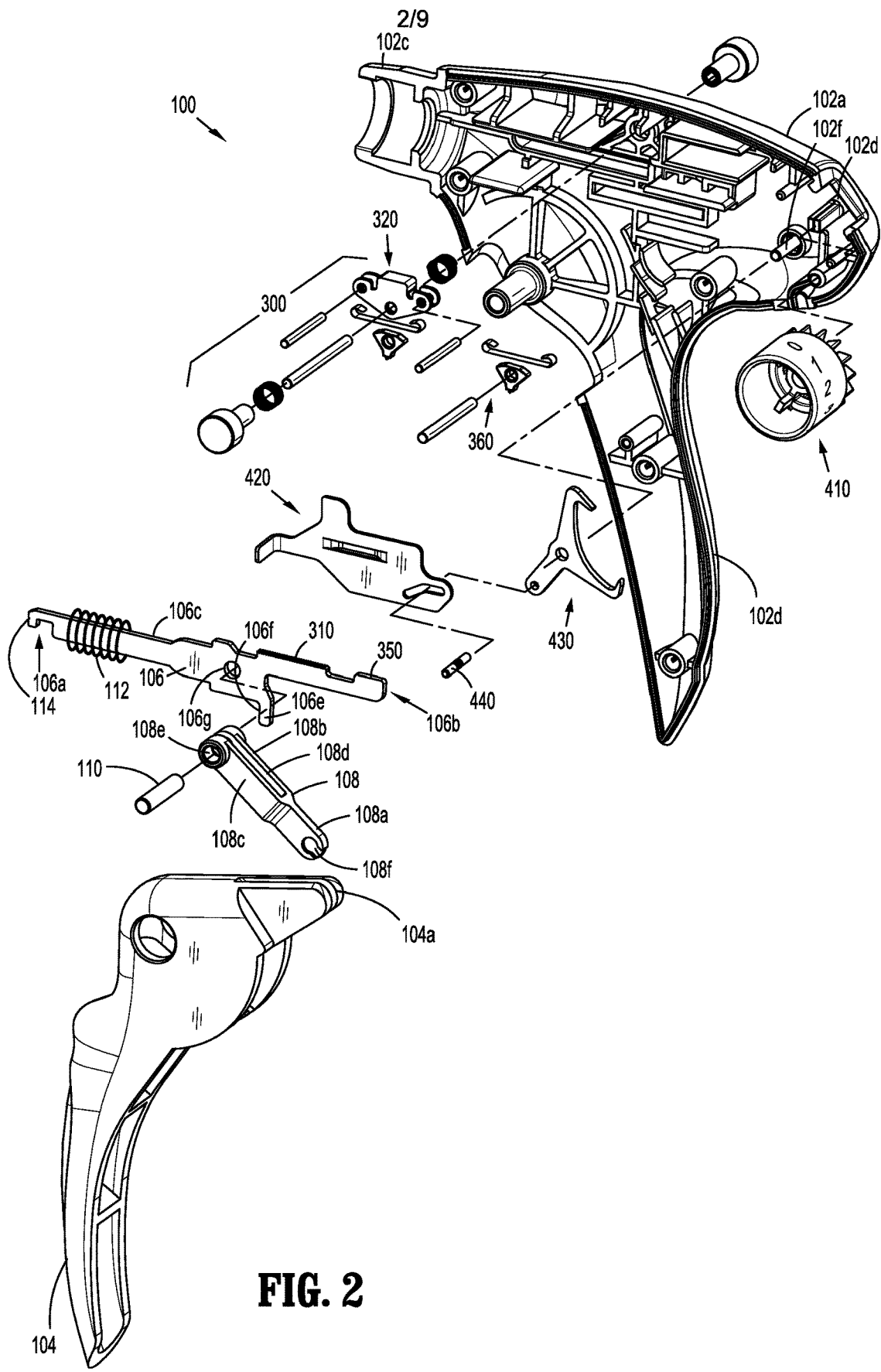
FIG. 2 is a perspective view, with parts separated, of the handle assembly of FIG. 1.

Referring now to FIGS. 1 and 2, an endoscopic surgical clip applier is provided in accordance with the present disclosure and generally identified by reference numeral 10. The surgical clip applier 10 generally includes a handle assembly 100 and an endoscopic assembly 200 that is selectively secured to the handle assembly 100 and extends distally therefrom. The endoscopic assembly 200 includes a hub assembly 210, a shaft assembly 220 extending from hub assembly 210, and a pair of jaws 250 pivotally connected to a distal end portion of the shaft assembly 220. In embodiments, at least one disposable surgical clip cartridge (not shown) may be selectively loadable into the shaft assembly 220 of the endoscopic assembly 200.

The handle assembly 100 of the surgical clip applier 10 includes a housing 102 having a first or right side half-section 102a and a second or left side half-section 102b. The housing 102 of the handle assembly 100 defines a nose 102c for supporting the hub assembly 210 of the endoscopic assembly 200, and a fixed handle 102d. It is contemplated that the housing 102 of the handle assembly 100 may be formed of a suitable polymer, such as a plastic or thermoplastic material, or may be formed from a metallic material such as stainless steel or the like.

The handle assembly 100 includes a trigger 104 pivotably supported between the right side half-section 102a and the left side half-section 102b of the housing 102. The trigger 104 is pivotably movable in a first direction such that the trigger 104 and the fixed handle 102d are approximated and pivotably movable in a second, opposite, direction such that the trigger 104 and the fixed handle 102d are spaced-apart.

A drive bar 106 (FIG. 2) is supported within the housing 102 of the handle assembly 100. The drive bar 106 may be a substantially flat member having a distal end portion 106a and a proximal end portion 106b. The distal end portion 106a of the drive bar 106 includes a hook member 114 that is provided to mate with a feature of the endoscopic assembly 200. The drive bar 106 defines an upper surface 106c and an opposite, lower surface 106d extending between the proximal and distal end portions 106a, 106b. The lower surface 106d of the drive bar 106 defines a protrusion 106e at a medial portion thereof and extending in a downward direction therefrom. The protrusion 106e defines a distal or leading surface 106f configured to selectively engage a portion of a counter switch, as will be described in further detail hereinbelow.

The drive bar 106 is operatively coupled to the trigger 104 and the pair of jaws 250 (FIG. 1) of the endoscopic assembly 200 to move the pair of jaws 250 between a spaced-apart configuration and an approximated configuration upon actuation of the trigger 104. Specifically, the handle assembly 100 includes a wishbone link 108 (FIG. 2) configured to couple the trigger 104 and the drive bar 106. The wishbone link 108 includes a first end portion having a tail 108a and a second end portion having a first arm 108b and a second arm 108c which are spaced apart to define a space 108d therebetween. The tail 108a of the wishbone link 108 is pivotably connected to the trigger 104 through a trigger slot 104a. Specifically, the tail 108a of the wishbone link 108 includes an opening 108f that is configured for pivotably locating a pin (not shown) defined within the trigger slot 104a. The space 108d between the first and second arms 108b, 108c of the wishbone link 108, and the drive bar 106, includes corresponding apertures 108e, 106g, respectively, which are configured to locate a drive bar pin 110 to pivotably connect the wishbone link 108 and the drive bar 106. The wishbone link 108 is configured to translate the pivotal movement of the trigger 104 into longitudinal movement of the drive bar 106, as will be described in further detail hereinbelow.

The drive bar 106 is configured to move one or more driving structures to load, and actuate the pair of jaws 250 to form a clip (not shown) fully or partially, and then reset to an initial position for the next clip application. To achieve this, a biasing member, such as, for example, a first return spring 112 is disposed to surround the drive bar 106 adjacent the distal end portion 106a such that, after the trigger 104 is actuated and the wishbone link 108 advances the drive bar 106 in a longitudinal or distal manner, the first return spring 112 is provided to return the drive bar 106 and the trigger 104 to its original position for the next clip application.

With continued reference to FIG. 2, the surgical clip applier 10 includes a ratchet assembly 300 disposed within the housing 102 of the handle assembly 100. The ratchet assembly 300 generally includes a first rack 310 disposed on the upper surface 106c of the drive bar 106 and a first pawl assembly 320 that is rotatably supported within the housing 102 of the handle assembly 100 and is operatively associated with the first rack 310. A second rack 350 is disposed on the upper surface 106c of the drive bar 106 proximal to, and spaced apart from, the first rack 310. A second pawl assembly 360 is rotatably supported within the housing 102 of the handle assembly 100 and is operatively associated with the second rack 350. The components of the ratchet assembly 300 cooperate to inhibit the trigger 104 from inadvertently returning to an unactuated position during a specific portion of the stroke. In one non-limiting embodiment, the ratchet assembly 300 inhibits the trigger 104 from returning to an unactuated position until a clip loaded into the pair of jaws 250 is partially formed, enough to be fired from the surgical clip applier 10, such that a new clip may be loaded into the pair of jaws 250 without an inadvertent double loading of clips into the pair of jaws 250.

For a more detailed description of the construction and operation of ratchet assembly 300, reference can be made to U.S. Provisional Patent Application No. 62/462,407 to Baril et al., titled "Endoscopic Surgical Clip Applier," filed on Feb. 23, 2017, the entire content of which is incorporated by reference herein.

A clip counting mechanism 400 is disposed within the handle assembly and includes a display gear 410, a counter switch 420, an escapement gear 430, and a gear pin 440. As illustrated in FIGS. 2, 3, 6A, and 6B, the display gear 410 defines a generally cylindrical profile, although any suitable profile may be utilized, such as square, oval, rectangular, octagonal, or the like. The display gear 410 defines opposed side surfaces 410a and 410b, which define a through-hole 412 (FIG. 6B) therethrough. The through-hole 412 is configured to be rotatably supported on a display gear post 102d (FIG. 2) extending from an interior surface of the right side half-section 102a of the housing 102. The side surface 410a of the display gear 410 defines a counterbore 414 (FIG. 6A) extending therethrough but not through the opposed side surface 410b. An outer surface 410c of the display gear 410 defines a plurality of concentrically disposed ratchet teeth 410d adjacent and through side surface 410b of the display gear 410. The plurality of ratchet teeth 410d are configured to selectively engage the escapement gear 430, as will be described in further detail hereinbelow. The outer surface 410c of the display gear 410 defines a plurality of numbers 416 sequentially arranged thereon. Each number of the plurality of numbers 416 is arranged around the circumference of the outer surface 410c such that the sequence of the plurality of numbers 416 is decreasing in nature as the display gear 410 rotates in a clockwise direction (e.g., 12-11-10-9-8, etc.), although it is contemplated that the sequence of the plurality of numbers 416 may increase as the drive gear 410 rotates in a clockwise direction. Each number of the plurality of numbers 416 is radially spaced apart by any suitable angle, and in one non-limiting embodiment each number of the plurality of numbers 416 is radially spaced apart at an angle of 24 degrees. In embodiments, the plurality of numbers 416 includes the numbers 3, 2, 1, and 0 to indicate that less than 4 clips remain in the endoscopic surgical clip applier 10. In this manner, the outer surface 410c of the display gear alerts the clinician to how many surgical clips remain in the endoscopic surgical clip applier 10.

To accommodate the radial spacing of 24 degrees between each number of the plurality of numbers 416, the plurality of ratchet teeth 410d includes 15 teeth, such that the display gear 410 rotates 24 degrees each time a clip is formed or fired, as will be described in further detail hereinbelow. As can be appreciated, it is contemplated that the plurality of teeth 410d may include any number of teeth corresponding to the radial angle defined between each number of the plurality of numbers, depending upon the needs of the procedure being performed.

Figure 9A:
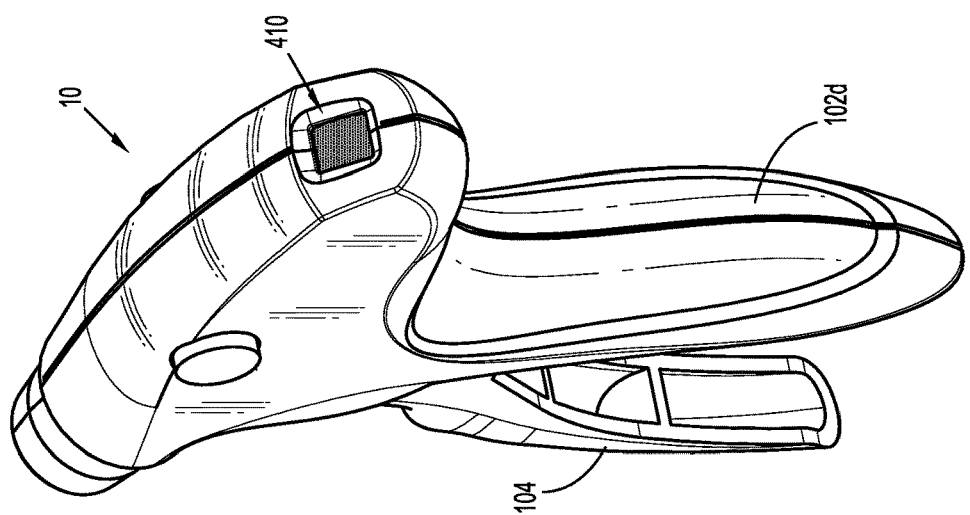
FIG. 9A is a perspective view of an indicator window of the clip counting mechanism of FIG. 3 shown in position where a clip cartridge of the endoscopic surgical clip applier of FIG. 1 is mostly full.
Figure 9B:
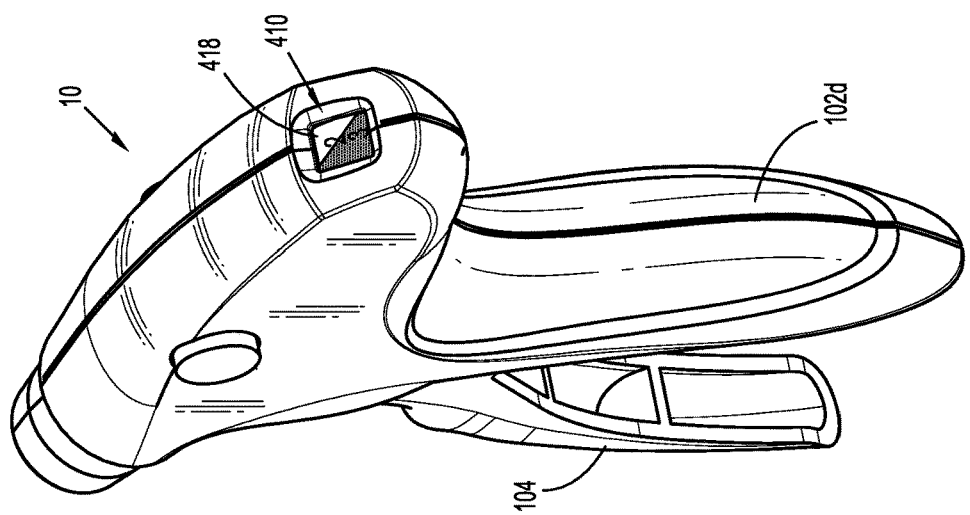
FIG. 9B is a perspective view of the indicator window of FIG. 9A, shown in a position where the clip cartridge of the endoscopic surgical clip applier of FIG. 1 is mostly empty.
Figure 9C:
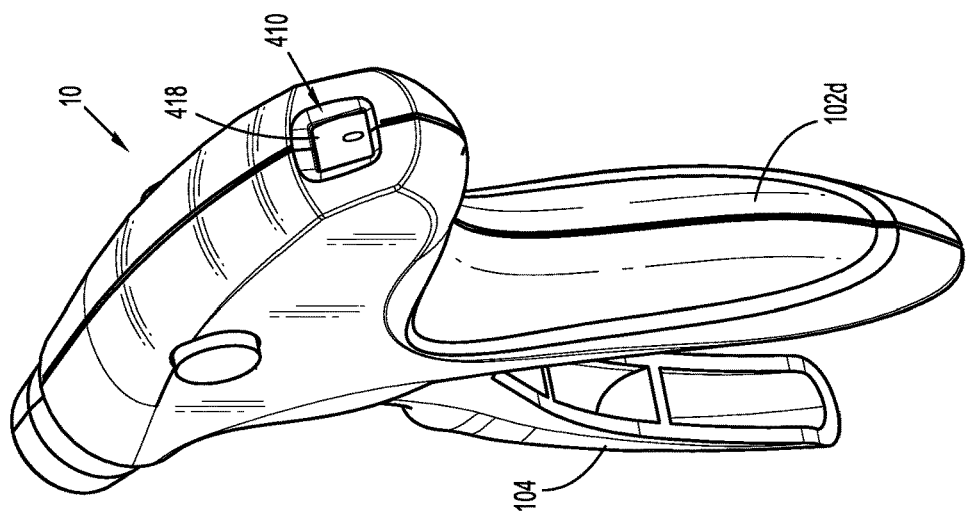
FIG. 9C is a perspective view of the indicator window of FIG. 9A, shown in a position where the clip cartridge of the endoscopic surgical clip applier of FIG. 1 is empty.

As illustrated in FIGS. 9A, 9B, and 9C, the outer surface 410c includes a contrasting color 418 disposed thereon that overlaps the numbers "0" and "1" of the plurality of numbers 416 and overlaps a portion of the number "2" of the plurality of numbers 416. Although generally illustrated as defining a diagonal line through the number "2" of the plurality of numbers 416, it is contemplated that the contrasting color 418 may define any suitable configuration such that the clinician is able to quickly ascertain the number of clips remaining in the clip stack (not shown). As can be appreciated, the contrasting color 418 may be any suitable color capable of grabbing the clinician's attention during a surgical procedure and may vary depending upon the needs of the procedure being performed (e.g., ambient lighting, background color, color blindness, etc.). In one non-limiting embodiment, the contrasting color 418 is red.

A biasing element 408 is in mechanical communication with the display gear 410 and rotatably biases the display gear 410 in a clockwise direction about the display gear post 102d of the right side-half section 102a (FIG. 2), although it is contemplated that the biasing element 408 may rotatably bias the display gear in a counterclockwise direction about the display gear post 102d. The biasing element 408 may rotatably bias the display gear 410 using any suitable means, such as being interposed between the display gear 410 and the right side-half section 102a, being disposed within the counterbore 414 of the display gear 410, disposed remote from the display gear 410, etc. In one non-limiting embodiment, the biasing element 408 is disposed within the counterbore 414 of the display gear 410 and is coaxially aligned with the display gear post 102d of the right side-half section 102a such that the biasing element 408 engages a portion of the display gear post 102d and a portion of the display gear 410. The biasing element 408 may be any suitable biasing element capable of rotatably biasing the display gear 410, such a constant force spring, torsion spring, balance spring, torsion bar, or the like. In one non-limiting embodiment, the biasing element 408 is a constant force spring disposed within the counterbore 414 of the display gear 410 and disposed about the display gear post 102d of the right side-half section 102a, such that the constant force spring engages a portion of each of the display gear 410 and the display gear post 102d.

Figure 3:
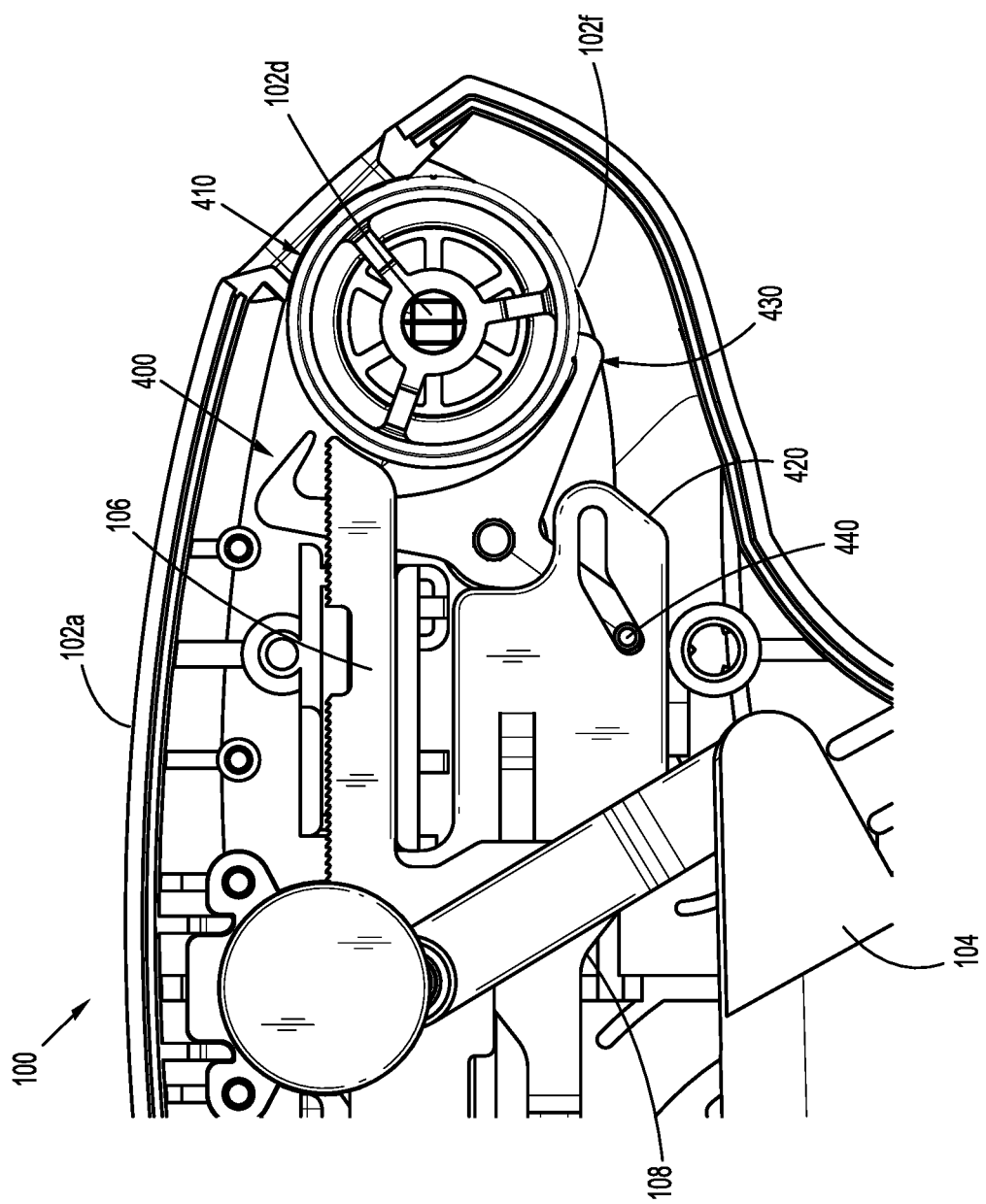
FIG. 3 is a side, cross-sectional view, of the handle assembly of FIG. 1, illustrating a clip counting mechanism in accordance with the present disclosure.
Figure 4:
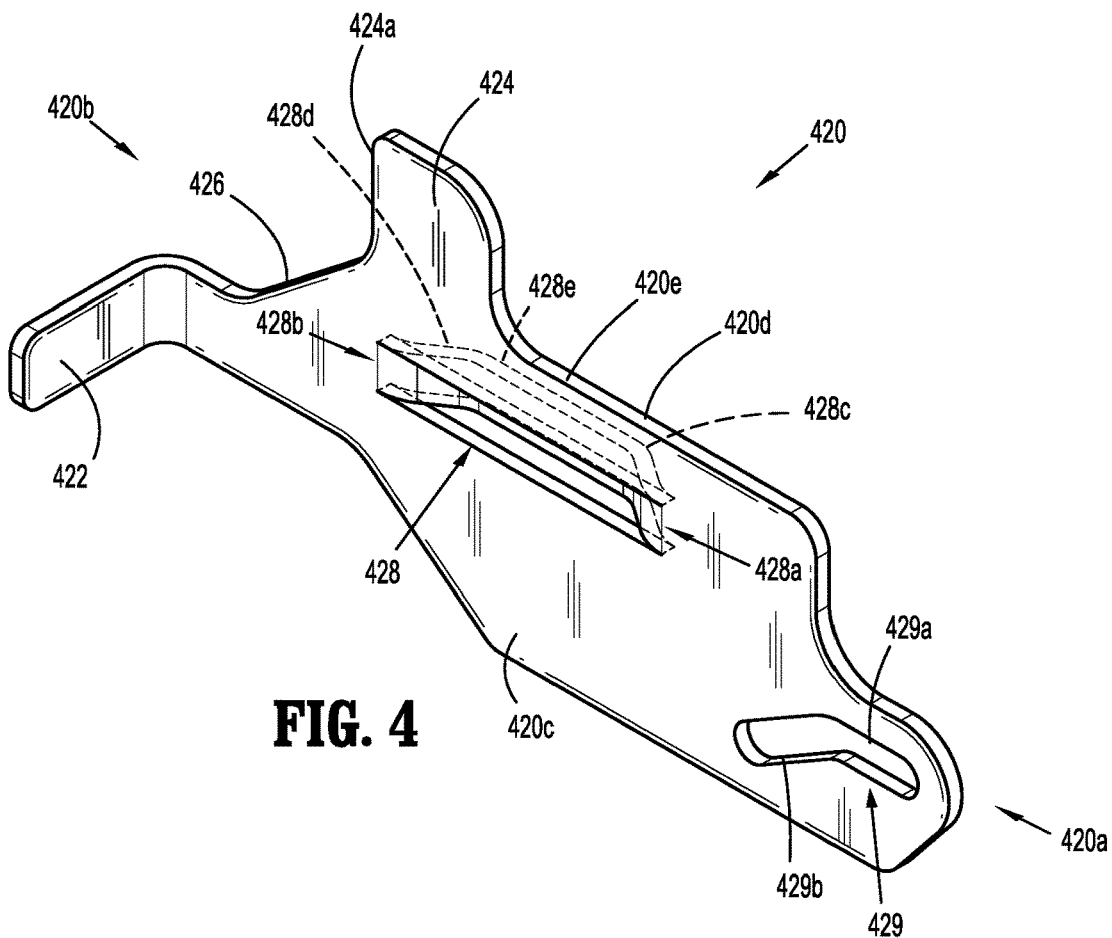
FIG. 4 is a perspective view of a counter switch of the clip counting mechanism of FIG. 3.

With reference to FIGS. 3 and 4, the counter switch 420 is reciprocally disposed within the housing 102 of the handle assembly 100 and defines a generally planar profile, although it is contemplated that any suitable profile may be utilized. The counter switch 420 defines a proximal end portion 420a and a distal end portion 420b opposite thereto and opposed side surfaces 420c and 420d extending therebetween. The counter switch 420 is interposed between the drive bar 106 and the right side half section 102a of the housing 102 (e.g., the side surface 420a is adjacent the drive bar 106 and the side surface 420b is adjacent the right side half section 102a). The side surface 420c defines a laterally extending tab 422 disposed adjacent the distal end portion 420b. Although generally shown as defining a right angle with respect to the side surface 420c of the counter switch 420, it is contemplated that the laterally extending tab 422 may define any suitable angle depending upon the location of the counter switch 420 within the housing 102, the stroke required to rotate the display gear 410, etc.

The counter switch 420 defines an upper surface 420e interposed between the opposed side surfaces 420c, 420d and extending between the proximal and distal end portions 420a, 420b. A medial portion of the upper surface 420e defines a vertically extending tab 424 and defines a leading or distal surface 424a configured to selectively engage the drive bar pin 110 (FIG. 2) on a return stroke, as will be described in further detail hereinbelow. The upper surface 420e defines a ramp or taper 426 interposed between the vertically extending tab and the laterally extending tab 422, such that the height of the counter switch 420 increases in a distal to proximal direction (e.g., in a direction from the distal end portion 420b to the proximal end portion 420a). In this manner, as the drive bar 106 is advanced in a distal direction, the drive bar pin 110 is free to translate relative to the counter switch 420 (e.g., the drive bar pin 110 does not contact the counter switch 420). However, as the drive bar 106 is retracted in a proximal direction, the drive bar pin 110 is inhibited from contacting the counter switch 420 until the leading surface 424a of the vertically extending tab 424 abuts the drive bar pin 110, and causes the counter switch 420 to translate in a proximal direction along with the drive bar 106 and drive bar pin 110.

The opposed side surfaces 420c, 420d of the counter switch 420 define a slot 428 having a proximal end portion 428a and a distal end portion 428b therethrough. The slot 428 extends in a proximal to distal direction along the counter switch 420, and in embodiments, the distal end portion 428a of the slot 428 is vertically aligned with the leading surface 424a of the vertically extending tab 424. The slot 428 defines a pair of tabs 428c and 428d at respective proximal and distal end portions 428a, 4268 thereof that extend from side surface 420b of the counter switch 420. In operation, the pair of tabs 428c, 428d serve as travel stops to define a maximum proximal travel distance and a maximum distal travel distance, as will be described in further detail hereinbelow. In embodiments, a bridge or connector 428e is interposed between the pair of tabs 428c, 428d and is configured to be slidably disposed within a corresponding channel (not shown) defined within the right side half section 102a.

The opposed side surfaces 420a, 420b of the counter switch 420 define a cam slot 429 therethrough adjacent to the proximal end portion 420a of the counter switch 420. The cam slot 429 includes a generally dogleg shaped profile having a proximal portion 429a and a distal portion 429b extending in a distal direction therefrom. The proximal portion 429a of the cam slot 429 is oriented in a horizontal manner (e.g., extends linearly along the counter switch 420 in a distal direction) and the distal portion 429b is oriented at an angle relative to the proximal portion 429a. Specifically, the distal portion 429b defines an obtuse angle relative to the proximal portion 429b and extends in a downward direction (e.g., away from the upper surface 420e of the counter switch 420). The cam slot 429 is configured to slidably receive the gear pin 440 therein, as will be described in further detail hereinbelow.

Figure 5:
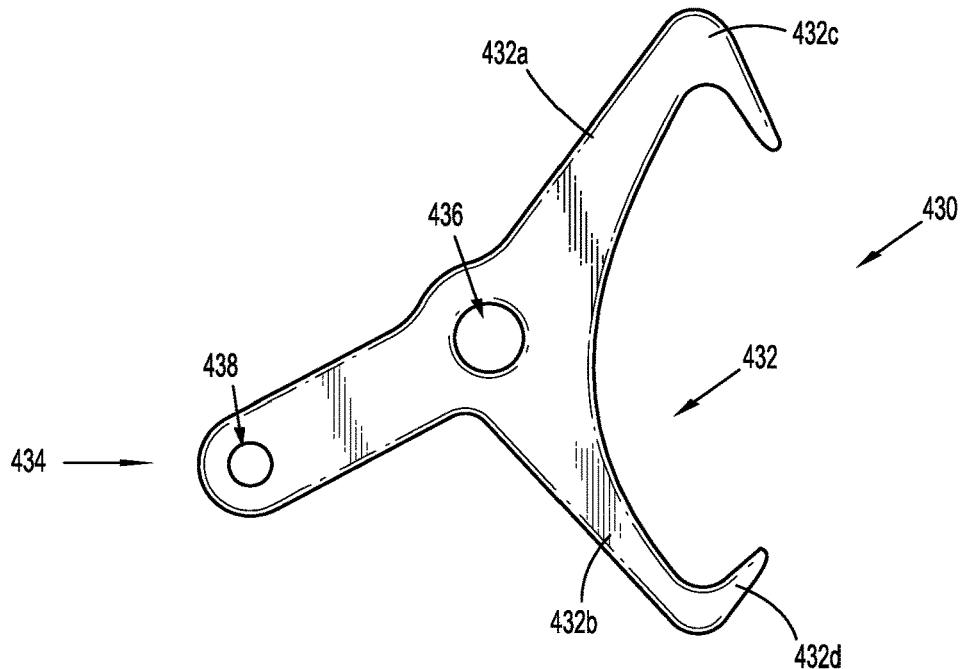
FIG. 5 is a side view of an escapement gear of the clip counting mechanism of FIG. 3.
Figure 6A:
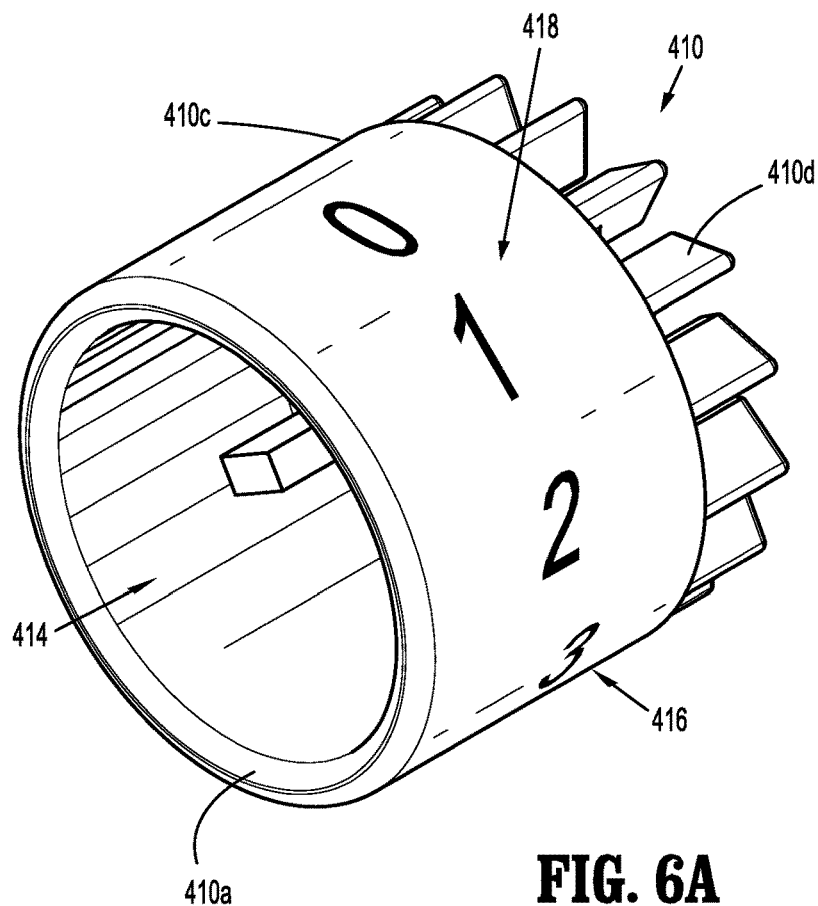
FIG. 6A is a perspective view of a display gear of the clip counting mechanism of FIG. 3.
Figure 6B:
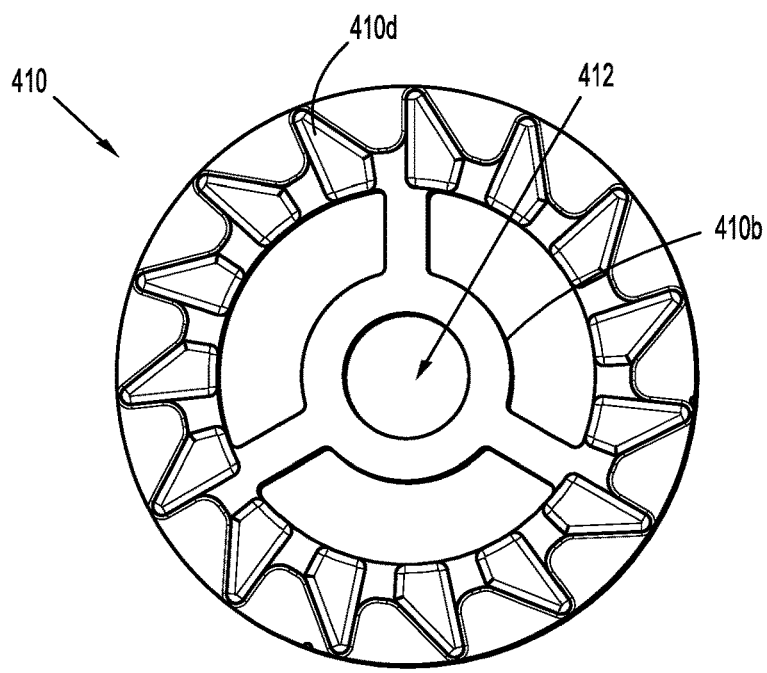
FIG. 6B is a side view of the display gear of FIG. 6A.

The escapement gear 430 (FIG. 5) defines a generally crescent wrench profile having a C-shaped proximal portion 432 and a rectangular shaped distal portion 434 extending distally therefrom. As best illustrated in FIG. 5, the distal portion 434 is oriented relative to the proximal portion 432 at a slight angle thereto (e.g., a centerline defined by the proximal portion 432 is not collinear with a centerline defined by the distal portion 434). In this manner, the C-shaped proximal portion 432 is able to straddle the plurality of ratchet teeth 410d (FIG. 6B) of the display gear 410, as will be described in further detail hereinbelow. The proximal portion 432 defines a pair of arms 432a and 432b that are arranged in a juxtaposed orientation. Each arm of the pair of arms 432a, 432b defines a respective tooth 432c and 432d oriented at a substantially perpendicular angle with respect to each respective arm 432a, 432b. As can be appreciated, it is contemplated that each tooth 432c, 432d may be oriented at any suitable angle with respect to each respective arm 432a, 432b, and may be disposed at the same angle or different angles than one another. The teeth 432c, 432d are configured to selectively engage a tooth of the plurality of ratchet teeth 410d of the display gear 410, as will be described in further detail hereinbelow.

The escapement gear 430 defines a bore 436 at a medial portion thereof that is configured to rotatably receive an escapement gear boss 102f (FIG. 2) therein that is defined on the right half section 102b of the housing 102. The distal portion 434 of the escapement gear 430 defines an aperture 438 therethrough configured to fixedly receive the gear pin 440 therein. As will be described in further detail hereinbelow, the gear pin 440 cams within the cam slot 428 of the counter switch 420 and the counter switch translates in a proximal or distal direction, causing the escapement gear 430 to rotate about the escapement gear boss 102f and selectively engage the display gear 410.

Figure 7C:
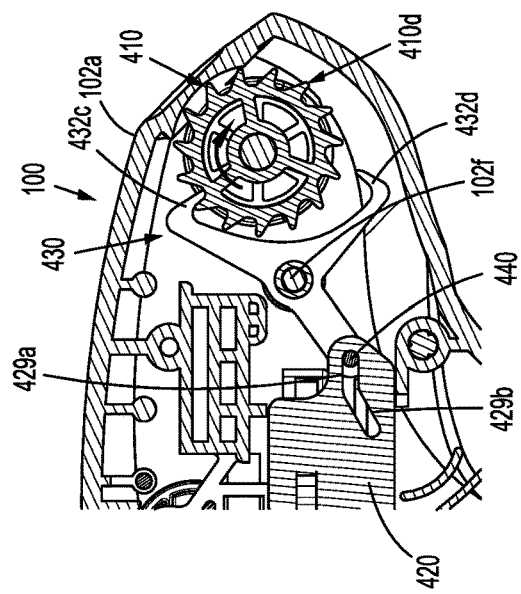
FIG. 7C is a side, cross-sectional view, of the handle assembly of FIG. 1, illustrating the clip counting mechanism of FIG. 3 in an advanced position, following complete actuation of the trigger.
Figure 7B:
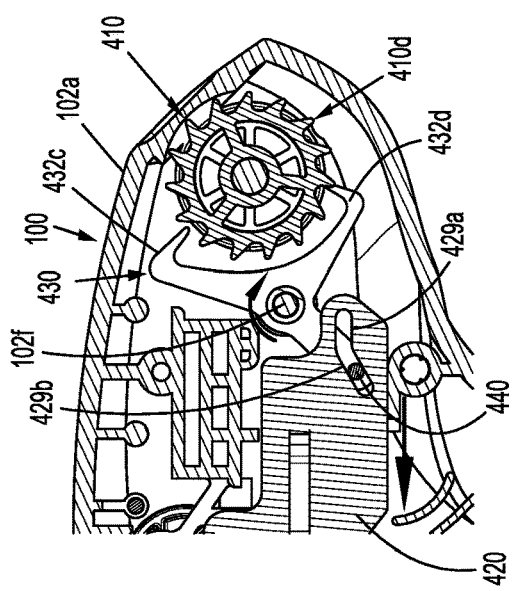
FIG. 7B is a side, cross-sectional view, of the handle assembly of FIG. 1, illustrating the clip counting mechanism of FIG. 3 in an intermediate, advanced position, during actuation of the trigger.
Figure 7A:
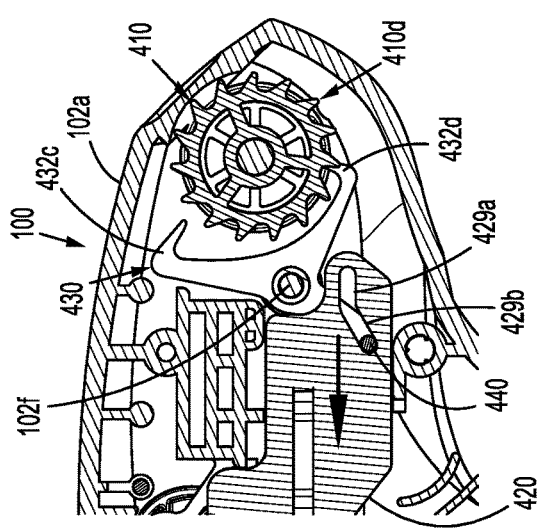
FIG. 7A is a side, cross-sectional view, of the handle assembly of FIG. 1, illustrating the clip counting mechanism of FIG. 3 in an initial, resting, position, prior to an actuation of a trigger.

In operation, with reference to FIGS. 7A-C, 8A-C, and 9A-C, as the clinician actuates the trigger 104 (FIG. 2) of the handle assembly 100 to fire or form a clip (not shown), the drive bar 106 is urged in a distal direction. With continued actuation of the trigger 104, the drive bar 106 translates further in a distal direction until the leading surface 106f of the protrusion 106e of the drive bar 106 engages the laterally extending tab 422 of the counter switch 420 (FIG. 7A). As the clinician further actuates the trigger 104, the drive bar continues to advance in a distal direction and begins to cam the gear pin 440 within the cam slot 429 of the counter switch 420 (FIG. 7B).

Camming of the gear pin 440 within the cam slot 429 causes the escapement gear 430 to rotate about the escapement gear boss 102f of the handle housing 102 in a clockwise direction (e.g., tooth 432c of arm 432a of the pair of arms rotates toward the display gear 410). In this manner, tooth 432d of arm 432b of the escapement gear 430 disengages from a tooth of the plurality of ratchet teeth 410d of the display gear 410. As the drive bar 106, and therefore the counter switch 420 are further urged in a distal direction, the escapement gear 430 is caused to rotate further in a clockwise direction until the tooth 432d of arm 432b disengages from the tooth of the plurality of ratchet teeth 410d of the display gear 410. Disengagement of the tooth of the plurality of ratchet teeth 410d enables the biasing element 408 to begin to rotate the display gear 410 about the display gear post 102d of the right side-half section 102a in a clockwise direction and begin incrementally changing the number of the plurality of numbers 416 of the display gear 410 that is displayed to the clinician. The display gear 410 continues to rotate in a clockwise direction about the display gear post 102d until continued distal advancement of the drive bar 106 and the counter switch 420 causes the tooth 432c of the escapement gear 430 to engage a tooth of the plurality of ratchet teeth 410d of the display gear 410 (FIG. 7C). At this point, the display gear 410 has rotated 12 degrees about display gear post 102d, and therefore has completed half of a full rotation of 24 degrees.

Figure 8C:
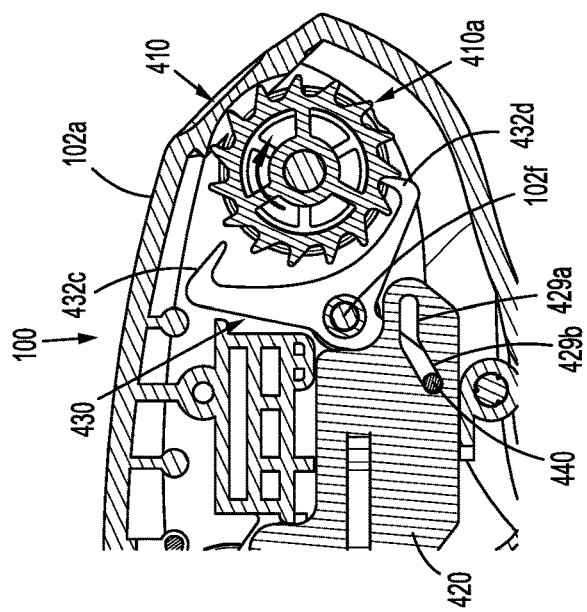
FIG. 8C is a side, cross-sectional view, of the handle housing of FIG. 1, illustrating the clip counting mechanism of FIG. 3 in a retracted position, following complete release of the trigger.
Figure 8B:
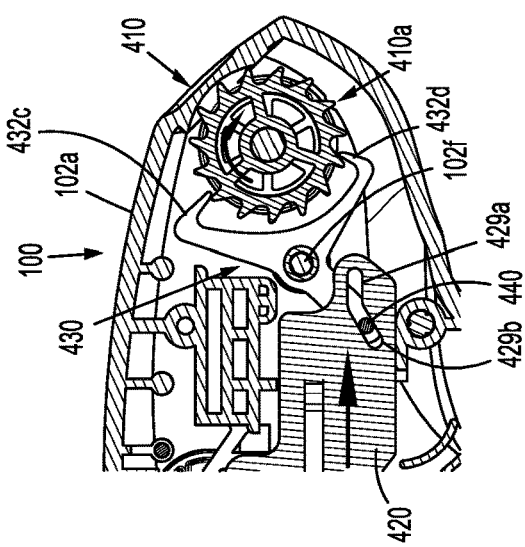
FIG. 8B is a side, cross-sectional view, of the handle assembly of FIG. 1, illustrating the clip counting mechanism of FIG. 3 in an intermediate, retracted position, during release of the trigger.
Figure 8A:
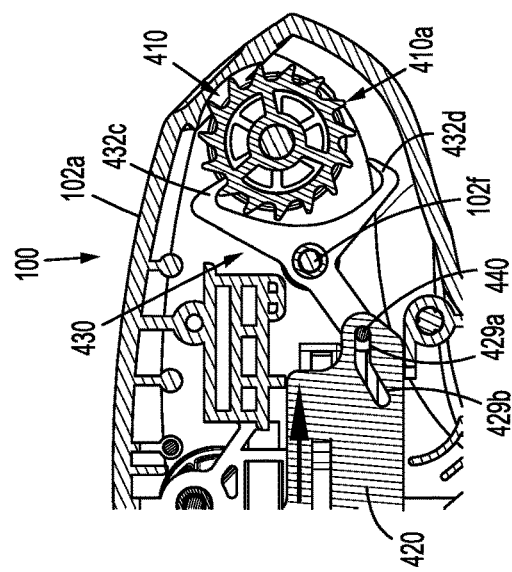
FIG. 8A is a side, cross-sectional view, of the handle assembly of FIG. 1, illustrating the clip counting mechanism of FIG. 3 in the advanced position, prior to a release of the trigger.

Once the clip has been fully formed, or racks 310, 350 have fully cleared respective pawls assemblies 320, 360, the clinician releases the trigger 104 which enables the drive bar 106, and therefore the counter switch 420, to begin returning to the initial, retracted position (FIG. 8A). Initial translation of the drive bar 106 in a proximal direction urges the counter switch 420 in a proximal direction thereby causing the gear pin 440 to cam within the cam slot 429 of the counter switch 420 (FIG. 8B). Camming of the gear pin 440 within the cam slot 429 while the counter switch 420 is translating in a proximal direction causes the escapement gear 430 to rotate about the escapement gear boss 102f of the handle housing 102 in a counter-clockwise direction (e.g., tooth 432d of arm 432b of the pair of arms rotates toward the display gear 410).

In this manner, escapement gear 430 rotates in an opposite direction to when the drive bar 106 is urged in a distal direction, thereby disengaging the tooth 432c of arm 432a from the plurality of ratchet teeth 410d of the display gear 410 and enabling the display gear 410 to rotate in a clockwise direction about the display gear post 102d. With continued proximal translation of the counter switch 420, the escapement gear 430 continues to rotate about the escapement gear boss 102f until tooth 432d of arm 432b of the escapement gear 430 engages a tooth of the plurality of ratchet teeth 410d of the display gear 410, thereby stopping rotation of the display gear 410 about the display gear post 102d (FIG. 8C). At this point, the display gear 410 has rotated a further 12 degrees about the display gear post 102d, such that the display gear 410 has rotated a total of 24 degrees during the full stroke of the surgical clip applier 10 to form or fire the surgical clip.

Each time the clinician wishes to fire or form a surgical clip, the above process is repeated until all of the remaining surgical clips have been fired or formed. As can be appreciated, the display gear 410 displays the number of surgical clips remaining to be fired and updates each time the clinician fires or forms a surgical clip using the above-described process. If the number of remaining surgical clips is 5 or greater, the outer surface 410c displays no contrasting color, and in embodiments, no numbers (FIG. 9A). If, during the surgical procedure, the number of remaining surgical clips is less than 4, then a portion of the outer surface 410c displays the contrasting color 418 (FIG. 9B), and the amount of the outer surface 410c displaying the contrasting color increases with the firing of each remaining surgical clip until the outer surface 410c entirely displays the contrasting color 418 to indicate that there are no surgical clip remaining (FIG. 9C).

Once the final surgical clip has been fired or formed, the surgical clip applier 10 engages a lockout mechanism (not shown) inhibiting the clinician from actuating the trigger 104.

Figure 10:
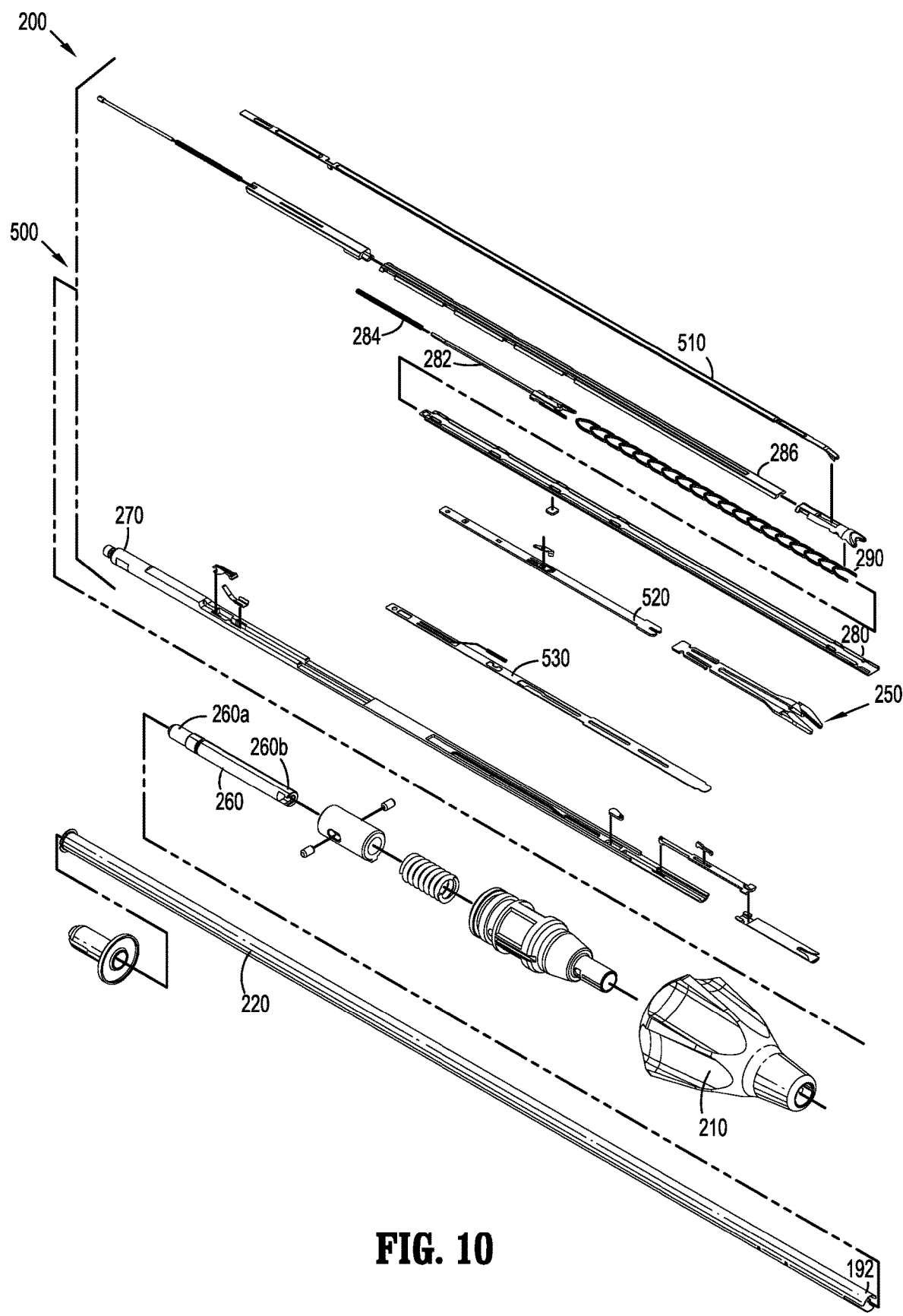
FIG. 10 is a perspective view of an endoscopic assembly of FIG. 1, with parts separated.

Turning now to FIG. 10, the endoscopic assembly 200 of the surgical clip applier includes a hub assembly 210, a shaft assembly 220, and the pair of jaws 250. The hub assembly 210 is rotatably mounted on a nose 102c (FIG. 2) of the housing 102 of the handle assembly 100 and is connected to a proximal end portion of the shaft assembly 220 to enable the shaft assembly 220 and the pair of jaws 250 to rotate three hundred and sixty degrees relative to a longitudinal center axis of the shaft assembly 220. The hub assembly 210 has a suitable configuration so as to be rotated simply by using a clinician's finger.

The endoscopic assembly 200 includes a spindle link 260 for operatively connecting the drive bar 106 to a driving mechanism 500 to move the pair of jaws 250 between the spaced-apart configuration and the approximated configuration upon actuation of the trigger 104. Specifically, the hook member 114 (FIG. 2) of the drive bar 106 is coupled to a first end portion 260a of the spindle link 260 and a spindle 270 of the drive mechanism 500 is coupled to a second end portion 206b of the spindle link 260. In this manner, translation of the drive bar 106 in a distal and proximal direction can thus advance and retract the spindle 270, respectively.

The drive mechanism 500 further includes an elongated clip channel member 280 for retaining a number of surgical clips 290 shown in an aligned manner above the clip channel member 280. A clip follower 282 and a clip follower spring 284 are provided to urge the surgical clips 290 distally through the elongated clip channel member 280. A channel cover 286 is provided to overlay the elongated clip channel member 280 and retain and guide the clip follower 282 and the clip follower spring 284 and the surgical clips 290 distally in the elongated clip channel member 280. The drive mechanism 500 also has a feed bar 510 for feeding the surgical clips 290 between the pair of jaws 250 and a filler component 520 and wedge plate 530.

For a more detailed description of the construction and operation of endoscopic assembly 200, reference can be made to U.S. Pat. No. 7,637,917 to Whitfield et al., the entire content of which is incorporated by reference herein.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A clip counting mechanism for use with a surgical clip applier, comprising:
   a display gear rotatably supported within a handle housing of a surgical clip applier and including an outer surface, the outer surface includes a plurality of numbers disposed thereon;
   a biasing element in mechanical communication with the display gear, the biasing element rotatably biasing the display gear;
   a counter switch reciprocally disposed within the handle housing and defining a proximal end portion and a distal end portion and opposed side surfaces extending therebetween, the opposed side surfaces defining a cam slot therethrough; and
   an escapement gear rotatably supported within the handle housing and defining a proximal end portion and a distal end portion, wherein the distal end portion is in mechanical communication with the cam slot of the counter switch and the proximal end portion is in mechanical communication with the display gear,
   wherein translation of the counter switch causes the cam slot to cam the escapement gear and selectively disengage the display gear and permit the display gear to rotate and selectively re-engage the display gear to inhibit rotation of the display gear, thereby enabling the display gear to rotate a predetermined angle of rotation.

2. The clip counting mechanism according to claim 1, wherein the outer surface of the display gear defines a plurality of ratchet teeth thereon.

3. The clip counting mechanism according to claim 2, wherein the escapement gear defines a pair of arms disposed in juxtaposed relation, each arm of the pair of arms defining respective first and second teeth.

4. The clip counting mechanism according to claim 3, wherein the first and second teeth are configured to selectively engage a respective tooth of the plurality of ratchet teeth.

5. The clip counting mechanism according to claim 2, wherein the plurality of ratchet teeth includes 15 teeth such that the pre-determined angle of rotation of the display gear is 24 degrees.

6. The clip counting mechanism according to claim 5, wherein translation of the counter switch in a first direction causes the display gear to rotate 12 degrees in a first direction.

7. The clip counting mechanism according to claim 6, wherein translation of the counter switch in a second direction causes the display gear to rotate a further 12 degrees in the first direction.

8. The clip counting mechanism according to claim 7, wherein each 24 degree rotation of the display gear in the first direction causes a different number of the plurality of numbers to be displayed to a clinician, the number displayed to the clinician being a number of surgical clips remaining within the surgical clip applier.

9. The clip counting mechanism according to claim 1, further including a gear pin fixedly secured to the escapement gear, the gear pin configured to be slidably received within the cam slot of the counter switch such that translation of the counter switch cams the gear pin within the cam slot, thereby causing the escapement gear to rotate.

10. The clip counting mechanism according to claim 1, wherein the biasing element is a constant-force spring.

11. An endoscopic surgical clip applier, comprising:
an endoscopic assembly; and
a handle assembly, including:
 a housing selectively connectable to the endoscopic assembly;
 a trigger pivotally connected to the housing;
 a drive bar translatably disposed within the housing of the handle assembly and operably coupled to the trigger; and
 a clip counting mechanism, including:
  a display gear rotatably supported within the handle housing of the surgical clip applier and including an outer surface, the outer surface includes a plurality of numbers disposed thereon;
  a biasing element in mechanical communication with the display gear, the biasing element rotatably biasing the display gear;
  a counter switch reciprocally disposed within the handle housing and defining a proximal end portion and a distal end portion and opposed side surfaces extending therebetween, the opposed side surfaces defining a cam slot therethrough, the counter switch operably coupled to the drive bar; and
  an escapement gear rotatably supported within the handle housing and defining a proximal end portion and a distal end portion, wherein the distal end portion is in mechanical communication with the cam slot of the counter switch and the proximal end portion is in mechanical communication with the display gear,
 wherein translation of the drive bar causes a corresponding translation of the counter switch, wherein translation of the counter switch causes the cam slot to cam the escapement gear and selectively disengage the display gear and permit the display gear to rotate and selectively re-engage the display gear to inhibit rotation of the display gear, thereby enabling the display gear to rotate a predetermined angle of rotation.

12. The endoscopic surgical clip applier according to claim 11, wherein the outer surface of the display gear defines a plurality of ratchet teeth thereon.

13. The endoscopic surgical clip applier according to claim 12, wherein the escapement gear defines a pair of arms disposed in juxtaposed relation, each arm of the pair of arms defining respective first and second teeth.

14. The endoscopic surgical clip applier according to claim 13, wherein the first and second teeth are configured to selectively engage a respective tooth of the plurality of ratchet teeth.

15. The endoscopic surgical clip applier according to claim 12, wherein the plurality of ratchet teeth includes 15 teeth such that the pre-determined angle of rotation of the display gear is 24 degrees.

16. The endoscopic surgical clip applier according to claim 15, wherein translation of the counter switch in a first direction causes the display gear to rotate 12 degrees in a first direction.

17. The endoscopic surgical clip applier according to claim 16, wherein translation of the counter switch in a second direction causes the display gear to rotate a further 12 degrees in the first direction.

18. The endoscopic surgical clip applier according to claim 17, wherein each 24 degree rotation of the display gear in the first direction causes a different number of the plurality of numbers to be displayed to a clinician, the number displayed to the clinician being a number of surgical clips remaining within the endoscopic surgical clip applier.

19. The endoscopic surgical clip applier according to claim 11, further including a gear pin fixedly secured to the escapement gear, the gear pin configured to be slidably received within the cam slot of the counter switch such that translation of the counter switch cams the gear pin within the cam slot, thereby causing the escapement gear to rotate.

20. The endoscopic surgical clip applier according to claim 11, wherein the biasing element is a constant-force spring.

* * * * *